(12) United States Patent
Seow et al.

(10) Patent No.: US 10,973,126 B2
(45) Date of Patent: *Apr. 6, 2021

(54) INSTRUMENT DRIVE UNITS

(71) Applicant: Covidien LP, Mansfield, MA (US)

(72) Inventors: Chi Min Seow, Watertown, MA (US); Jaimeen Kapadia, Cambridge, MA (US); Richard S. Lech, Hamden, CT (US); Michael Zemlok, Prospect, CT (US); Mark H. Macleod, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,866

(22) Filed: Jul. 6, 2020

(65) Prior Publication Data

US 2020/0337153 A1 Oct. 22, 2020

Related U.S. Application Data

(63) Continuation of application No. 16/304,372, filed as application No. PCT/US2017/034394 on May 25, 2017, now Pat. No. 10,736,219.

(Continued)

(51) Int. Cl.
*H05K 1/14* (2006.01)
*A61B 34/30* (2016.01)
(Continued)

(52) U.S. Cl.
CPC ............. *H05K 1/148* (2013.01); *A61B 34/30* (2016.02); *A61B 34/35* (2016.02); *B25J 9/12* (2013.01);
(Continued)

(58) Field of Classification Search
CPC .......... H02K 2203/03; H02K 2207/03; H02K 11/30; H02K 11/33; H05K 1/14;
(Continued)

(56) References Cited

U.S. PATENT DOCUMENTS

| | | | |
|---|---|---|---|
| 2,602,308 A | 7/1952 | Bonnet | |
| 2,958,013 A | * 10/1960 | Ansley | ................... H05K 3/366 |
| | | | 361/736 |

(Continued)

FOREIGN PATENT DOCUMENTS

| | | |
|---|---|---|
| CN | 102014759 A | 4/2011 |
| CN | 104584530 A | 4/2015 |

(Continued)

OTHER PUBLICATIONS

Chinese Office Action dated Nov. 4, 2020, issued in corresponding Chinese Appln. No. 201780032091, 10 pages.

(Continued)

*Primary Examiner* — Burton S Mullins

(57) ABSTRACT

An integrated circuit includes a nexus and a first, a second, a third, and a fourth circuit board. Each of the first and second circuit boards is coupled to opposing sides of the nexus, and each of the third and fourth circuit boards is coupled to opposing sides of the second circuit board. The integrated circuit is transitionable between a first, open configuration, in which the first, second, third and fourth circuit boards and the nexus are substantially coplanar, and a second configuration, in which the first, second, third and fourth circuit boards and the nexus are coupled to one another to define a cavity therein.

18 Claims, 7 Drawing Sheets

Related U.S. Application Data

(60) Provisional application No. 62/342,003, filed on May 26, 2016.

(51) Int. Cl.

| | | |
|---|---|---|
| *A61N 1/00* | (2006.01) | |
| *H02K 11/30* | (2016.01) | |
| *H02K 11/33* | (2016.01) | |
| *A61B 34/35* | (2016.01) | |
| *B25J 9/12* | (2006.01) | |
| *H02K 5/20* | (2006.01) | |
| *H02K 5/22* | (2006.01) | |
| *H05K 1/02* | (2006.01) | |
| *A61B 17/00* | (2006.01) | |
| *H05K 1/18* | (2006.01) | |

(52) U.S. Cl.
CPC .............. *H02K 5/20* (2013.01); *H02K 5/225* (2013.01); *H02K 11/33* (2016.01); *H05K 1/0201* (2013.01); *H05K 1/028* (2013.01); *A61B 2017/00477* (2013.01); *H02K 2205/09* (2013.01); *H02K 2211/03* (2013.01); *H05K 1/147* (2013.01); *H05K 1/18* (2013.01); *H05K 2201/047* (2013.01); *H05K 2201/10189* (2013.01); *H05K 2201/2018* (2013.01)

(58) Field of Classification Search
CPC ........ H05K 1/118; H05K 1/141; H05K 1/147; H05K 1/148; H05K 3/361; H05K 3/366; H05K 3/368; A61N 1/00; A61B 34/30
See application file for complete search history.

(56) References Cited

U.S. PATENT DOCUMENTS

| | | | |
|---|---|---|---|
| 3,583,139 A | | 6/1971 | Purrer |
| 4,513,064 A | * | 4/1985 | Marcus .................... H05K 7/14 428/582 |
| 4,897,014 A | | 1/1990 | Tietze |
| 4,990,948 A | | 2/1991 | Sasaki |
| 5,008,496 A | * | 4/1991 | Schmidt ............... H05K 1/0278 174/254 |
| 5,093,985 A | * | 3/1992 | Houldsworth ......... H05K 1/148 29/622 |
| 5,296,831 A | * | 3/1994 | Suzuki ................. G11B 7/0935 174/254 |
| 5,495,076 A | * | 2/1996 | Davis ................. B60R 16/0215 174/250 |
| 5,748,767 A | | 5/1998 | Raab |
| 5,762,458 A | | 6/1998 | Wang et al. |
| 5,826,126 A | | 10/1998 | Nomura |
| 5,921,992 A | | 7/1999 | Costales et al. |
| 6,016,253 A | * | 1/2000 | Seitz ...................... H05K 1/028 174/117 F |
| 6,016,448 A | | 1/2000 | Busacker et al. |
| 6,063,095 A | | 5/2000 | Wang et al. |
| 6,076,525 A | | 6/2000 | Hoffman |
| 6,306,126 B1 | | 10/2001 | Moctezuma |
| 6,331,181 B1 | | 12/2001 | Tierney et al. |
| 6,416,415 B1 | | 7/2002 | Yu |
| 6,665,191 B2 | | 12/2003 | Blood |
| 6,778,389 B1 | * | 8/2004 | Glovatsky ............ H01L 25/065 165/80.1 |
| 6,788,018 B1 | | 9/2004 | Blumenkranz |
| 6,824,471 B2 | | 11/2004 | Kamenov |
| 6,994,708 B2 | | 2/2006 | Manzo |
| 6,996,487 B2 | | 2/2006 | Jutras et al. |
| 7,035,716 B2 | | 4/2006 | Harris et al. |
| 7,118,564 B2 | | 10/2006 | Ritchie et al. |
| 7,524,320 B2 | | 4/2009 | Tierney et al. |
| 7,722,607 B2 | | 5/2010 | Dumbauld et al. |
| 7,809,184 B2 | | 10/2010 | Neubauer et al. |
| 7,947,051 B2 | | 5/2011 | Lee et al. |
| 7,954,397 B2 | | 6/2011 | Choi et al. |
| 7,963,913 B2 | | 6/2011 | Devengenzo et al. |
| 7,979,157 B2 | | 7/2011 | Anvari |
| 8,021,326 B2 | | 9/2011 | Moll et al. |
| 8,183,520 B2 | | 5/2012 | Prisco |
| 8,392,022 B2 | | 3/2013 | Ortmaier et al. |
| 8,394,054 B2 | | 3/2013 | Wallace et al. |
| 8,479,969 B2 | | 7/2013 | Shelton, IV |
| 8,506,557 B2 | | 8/2013 | Zemlok et al. |
| 8,525,687 B2 | | 9/2013 | Tran |
| 8,828,023 B2 | | 9/2014 | Neff et al. |
| 8,992,113 B2 | | 3/2015 | Campagna et al. |
| 10,736,219 B2 | * | 8/2020 | Seow .................... H05K 1/148 |
| 2001/0008343 A1 | | 7/2001 | Herdin et al. |
| 2003/0040758 A1 | | 2/2003 | Wang et al. |
| 2004/0054489 A1 | | 3/2004 | Moctezuma De La Barrera et al. |
| 2004/0128026 A1 | | 7/2004 | Harris et al. |
| 2004/0143243 A1 | | 7/2004 | Wahrburg |
| 2004/0254680 A1 | | 12/2004 | Sunaoshi |
| 2005/0113815 A1 | | 5/2005 | Ritchie et al. |
| 2005/0116673 A1 | | 6/2005 | Carl et al. |
| 2006/0264742 A1 | | 11/2006 | Neubauer et al. |
| 2007/0035203 A1 | | 2/2007 | Bromfield |
| 2008/0058861 A1 | | 3/2008 | Cooper et al. |
| 2008/0065105 A1 | | 3/2008 | Larkin et al. |
| 2008/0103491 A1 | | 5/2008 | Omori et al. |
| 2008/0228195 A1 | | 9/2008 | von Jako et al. |
| 2008/0262513 A1 | | 10/2008 | Stahler et al. |
| 2009/0036902 A1 | | 2/2009 | DiMaio et al. |
| 2009/0040736 A1 | * | 2/2009 | Becherer ................. H05K 1/14 361/749 |
| 2009/0044655 A1 | | 2/2009 | DeLouis et al. |
| 2009/0163930 A1 | | 6/2009 | Aoude et al. |
| 2009/0171197 A1 | | 7/2009 | Burger et al. |
| 2009/0326324 A1 | | 12/2009 | Munoz Martinez et al. |
| 2010/0082041 A1 | | 4/2010 | Prisco |
| 2010/0286712 A1 | | 11/2010 | Won et al. |
| 2010/0318101 A1 | | 12/2010 | Choi |
| 2010/0332031 A1 | | 12/2010 | Itkowitz et al. |
| 2011/0015650 A1 | | 1/2011 | Choi et al. |
| 2011/0015850 A1 | | 1/2011 | Tange et al. |
| 2011/0022060 A1 | | 1/2011 | Won et al. |
| 2011/0190937 A1 | | 8/2011 | Ortmaier |
| 2011/0224825 A1 | | 9/2011 | Larkin et al. |
| 2011/0290856 A1 | | 12/2011 | Shelton, IV et al. |
| 2012/0029694 A1 | | 2/2012 | Muller |
| 2012/0041263 A1 | | 2/2012 | Sholev |
| 2012/0116416 A1 | | 5/2012 | Neff et al. |
| 2012/0143211 A1 | | 6/2012 | Kishi |
| 2012/0289973 A1 | | 11/2012 | Prisco et al. |
| 2013/0096575 A1 | | 4/2013 | Olson |
| 2013/0123783 A1 | | 5/2013 | Marczyk et al. |
| 2013/0131651 A1 | | 5/2013 | Strobl et al. |
| 2013/0144307 A1 | | 6/2013 | Jeong et al. |
| 2013/0193898 A1 | | 8/2013 | Williams et al. |
| 2013/0218024 A1 | | 8/2013 | Boctor et al. |
| 2013/0304086 A1 | | 11/2013 | Tovey et al. |
| 2013/0325033 A1 | | 12/2013 | Schena et al. |
| 2014/0001234 A1 | | 1/2014 | Shelton, IV et al. |
| 2014/0005677 A1 | | 1/2014 | Shelton, IV et al. |
| 2014/0046340 A1 | | 2/2014 | Wilson et al. |
| 2014/0100587 A1 | | 4/2014 | Farritor et al. |
| 2014/0110453 A1 | | 4/2014 | Wingardner et al. |
| 2014/0252071 A1 | | 9/2014 | Moore et al. |
| 2016/0294092 A1 | | 10/2016 | Kikuchi et al. |
| 2016/0338781 A1 | | 11/2016 | Kapadia |
| 2017/0071692 A1 | | 3/2017 | Taylor et al. |
| 2017/0104906 A1 | | 4/2017 | Tang |
| 2018/0008338 A1 | | 1/2018 | Kopp |

FOREIGN PATENT DOCUMENTS

| | | | |
|---|---|---|---|
| DE | 102004012783 A1 | | 10/2005 |
| DE | 102005032964 A1 * | 1/2006 | ............ H02K 11/00 |
| DE | 202008009571 U1 | | 10/2008 |
| DE | 102010062759 A1 * | 6/2012 | ............ H05K 1/14 |
| DE | 102014203921 A1 | | 9/2015 |
| EP | 2772206 A2 | | 9/2014 |

(56) References Cited

FOREIGN PATENT DOCUMENTS

| KR | 20090089558 | A  | 8/2009  |
|----|-------------|----|---------|
| WO | 9937220     | A1 | 7/1999  |
| WO | 2006079108  | A1 | 7/2006  |
| WO | 2009151205  | A1 | 12/2009 |
| WO | 2010068005  | A2 | 6/2010  |
| WO | 2010126127  | A1 | 11/2010 |
| WO | 2012112888  | A2 | 8/2012  |
| WO | 2013159933  | A1 | 10/2013 |
| WO | 2015196489  | A1 | 12/2015 |

OTHER PUBLICATIONS

European Search Report dated Aug. 24, 2017, corresponding to European Application No. 14881189.6; 13 pages.
Chinese Office Action (with English translation) dated Jul. 20, 2018, corresponding to Chinese Application No. 201480073374.4; 29 total pages.
European Office Action dated Aug. 7, 2018, corresponding to European Application No. 14 881 189.6; 8 pages.
European Search Report dated Sep. 6, 2018, corresponding to European Application No. 16752762.1; 11 pages.
European Search Report dated Dec. 20, 2017, corresponding to European Application No. 15793145.2; 9 total pages.
European Search Report dated Dec. 7, 2017, corresponding to European Application No. 15792219.6; 11 pages.
Chinese Office Action (with English tranlsation) dated Aug. 21, 2018, corresponding to Chinese Application No. 201580025231.0; 15 total pages.
International Search Report for PCT/US2014/064472 dated Feb. 13, 2015 (5 pages).
International Search Report for PCT/US2016/014002, dated Mar. 21, 2016 (4 pages).
International Search Report for PCT/US2015/027905, dated Jul. 28, 2015 (2 pages).
European Search Report dated Dec. 20, 2019, corresponding to counterpart European Application No. 17803553.1; 7 pages.

* cited by examiner

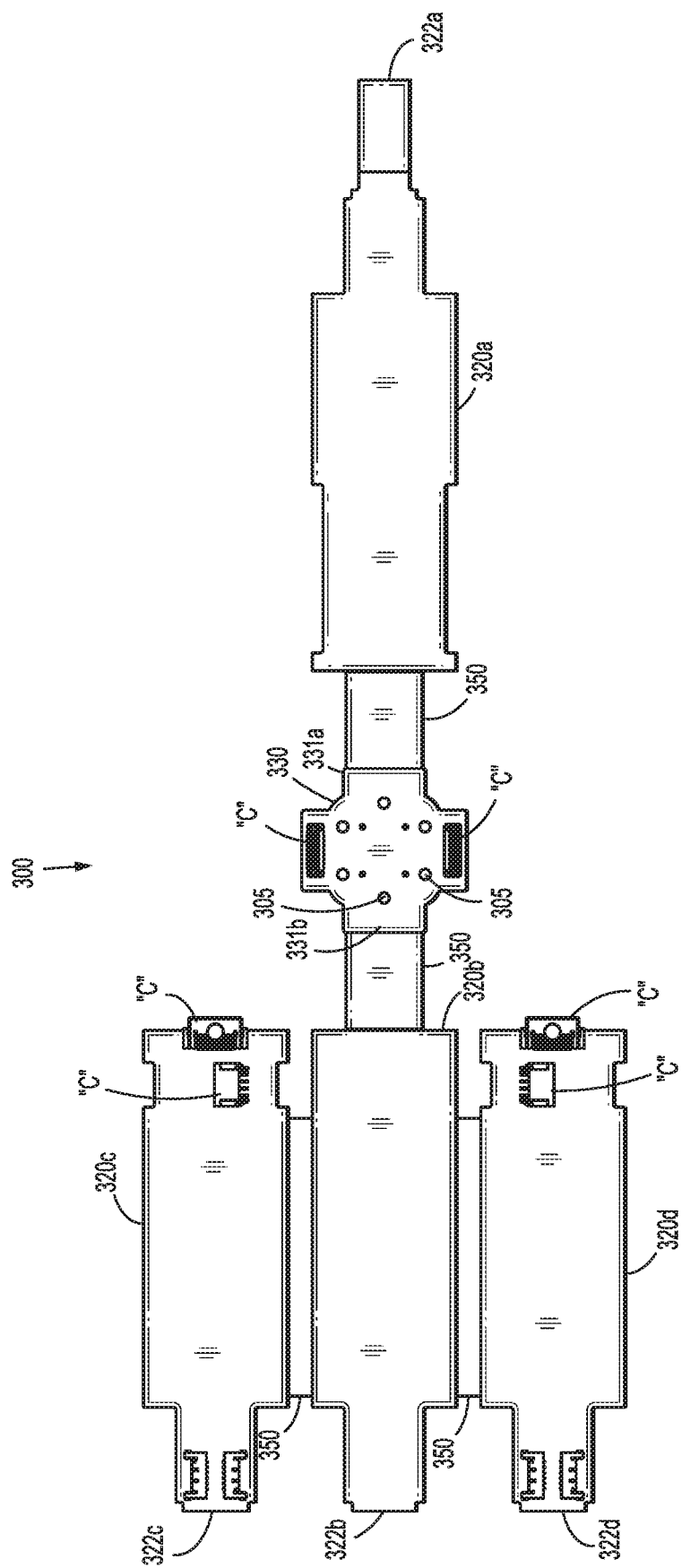

INSTRUMENT DRIVE UNITS

CROSS-REFERENCE TO RELATED APPLICATIONS

This application is a Continuation Application of U.S. patent application Ser. No. 16/304,372, filed on Nov. 26, 2018, which is a U.S. National Stage Application filed under 35 U.S.C. § 371(a) of International Patent Application No. PCT/US2017/034394, filed May 25, 2017, which claims the benefit of and priority to U.S. Provisional Patent Application No. 62/342,003, filed May 26, 2016, the entire contents of each of which are incorporated by reference herein.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement.

Manually-operated surgical instruments often include a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument.

The instrument drive unit includes a number of internal components, such as a motor pack and corresponding control circuitry. As a result of the instrument drive unit's complex design, there is a need for space saving internal components which provide for expeditious manufacturing, assembly, and testing of internal components and overall assemblies, and facilitation of heat dissipation, while still providing for a robust and durable assembly.

SUMMARY

In accordance with an aspect of the present disclosure, an integrated circuit is provided. The integrated circuit includes a nexus and a first, second, third, and fourth circuit board. Each of the first and second circuit boards are electrically and mechanically coupled to the nexus on opposing sides thereof. Each of the third and fourth circuit boards are electrically and mechanically coupled to the first circuit board on opposing sides thereof. The integrated circuit is transitionable between a first, open configuration, in which the first, second, third and fourth circuit boards and the nexus are substantially coplanar, and a second configuration, in which the first, second, third and fourth circuit boards and the nexus are coupled to one another to define a cavity therein.

In an embodiment, the cavity is configured to receive a motor assembly of a motor pack. It is contemplated that in the second configuration of the integrated circuit a longitudinal axis defined by the cavity may be transverse to a plane defined by the nexus. It is further envisioned that the nexus, the first circuit board, the second circuit board, the third circuit board, and the fourth circuit board may be printed circuit boards. Further still, at least one of the nexus, the first circuit board, the second circuit board, the third circuit board, or the fourth circuit board may define at least one ventilation hole therethrough.

In a further embodiment, at least one of the nexus, the first circuit board, the second circuit board, the third circuit board, or the fourth circuit board may include at least one electrical connector configured to electrically interconnect the nexus, the first circuit board, the second circuit board, the third circuit board, or the fourth circuit board to electrical components of the instrument drive unit. Further still, in an embodiment a proximal end of the first circuit board and a proximal end of the second circuit board may each be mechanically and electrically coupled with the nexus.

It is further envisioned that a distal end of each of the first circuit board, the second circuit board, the third circuit board, and the fourth circuit board may be configured to selectively mechanically and electrically engage a motor assembly of a motor pack of the instrument drive unit. Further, the distal ends of each of the first circuit board, the second circuit board, the third circuit board, and the fourth circuit board may be configured to selectively mechanically and electrically engage a distal mounting flange of the motor assembly.

In another embodiment of the present disclosure an instrument drive unit is provided which includes an instrument drive unit holder and an instrument drive unit. The instrument drive unit holder is configured to be selectively coupled to a robotic arm. The instrument drive unit is selectively couplable to the instrument drive unit holder. The instrument drive unit includes a housing cover selectively engagable with the instrument drive unit holder and a motor pack. The motor pack includes an integrated circuit and a motor assembly. The integrated circuit includes a first circuit board and a second circuit board each of which are electrically and mechanically coupled to opposing sides of a nexus, and a third circuit board and a fourth circuit board each of which are electrically and mechanically coupled to opposing sides of the first circuit board. The motor assembly includes a proximal mounting cap, a constrainer, a distal mounting flange, and at least one motor. The proximal mounting cap is nestable upon the nexus of the integrated circuit, and the constrainer is nestable upon the proximal mounting cap.

The integrated circuit is transitionable between a first, open configuration, in which the first, second, third and fourth circuit boards and the nexus are substantially coplanar, and a second configuration, in which the first, second, third and fourth circuit boards and the nexus are coupled to one another to define a cavity therein.

In an embodiment, in the second configuration of the integrated circuit, a longitudinal axis defined by the cavity may be transverse to a plane defined by the nexus. In a further embodiment, a distal end of at least one circuit board may be configured to selectively mechanically and electrically engage a corresponding elastomeric isolator disposed on the distal mounting flange of the motor assembly.

In yet another embodiment, a distal end of each of the first circuit board, the second circuit board, the third circuit board, and the fourth circuit board may be configured to selectively mechanically and electrically engage a first, second, third, and fourth elastomeric isolator disposed on the distal mounting flange of the motor assembly.

In a further embodiment, a proximal end of the first circuit board and a proximal end of the second circuit board may each be mechanically and electrically coupled with the nexus. Further, the nexus, the first circuit board, the second circuit board, the third circuit board, and the fourth circuit board may be printed circuit boards. Further still, in an embodiment at least one of the nexus, the first circuit board, the second circuit board, the third circuit board, or the fourth circuit board may define at least one ventilation hole therethrough.

In an embodiment at least one of the nexus, the first circuit board, the second circuit board, the third circuit board, or the fourth circuit board may include at least one electrical connector configured to electrically interconnect the nexus, the first circuit board, the second circuit board, the third circuit board, or the fourth circuit board with electrical components of the instrument drive unit.

In yet another aspect of the present disclosure, an instrument drive unit is provided and includes a motor assembly, and an integrated circuit. The integrated circuit includes a nexus and first and second elongated circuit boards pivotably coupled to the nexus between a first configuration, in which the nexus and the first and second circuit boards are substantially coplanar, and a second configuration, in which the nexus and the first and second circuit boards cooperatively assume a three dimensional configuration to define a cavity configured for receipt of the motor assembly.

In some embodiments, the integrated circuit may further include third and fourth elongate circuit boards electrically and mechanically coupled to the second circuit board and disposed in parallel relation with the second circuit board. In the first configuration, a proximal end of each of the third and fourth circuit boards may be unconnected to the nexus, and in the second configuration, the proximal end of each of the third and fourth circuit boards may be connected to the nexus.

BRIEF DESCRIPTION OF THE DRAWINGS

Embodiments of the present disclosure are described herein with reference to the accompanying drawings, wherein:

FIG. 5 is a top view of the integrated circuit of the motor pack of the instrument drive unit of FIG. 3 with the integrated circuit in a first configuration.

DETAILED DESCRIPTION

Figure 1:
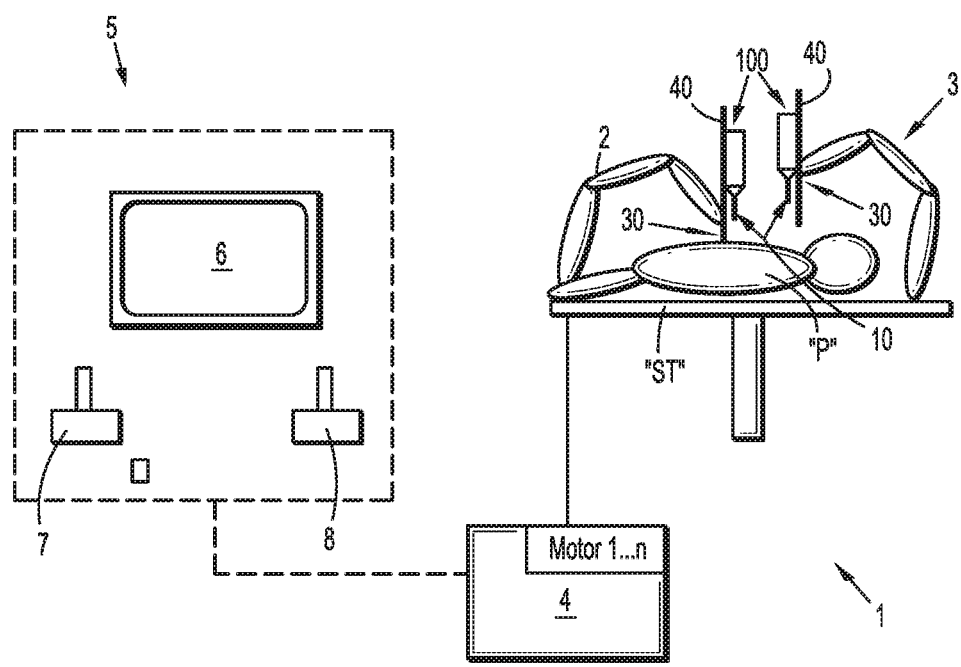
FIG. 1 is a schematic illustration of a robotic surgical system including a surgical assembly in accordance with the present disclosure.

As will be described in detail below, embodiments of the present disclosure describe a surgical assembly configured to be attached to a surgical robotic arm. The surgical assembly includes a motor pack utilized to drive an instrument drive unit for driving the operation of a surgical instrument, and more specifically an integrated circuit of the motor pack having a specific manufacturing and assembly configuration, and methods thereof are described in detail with reference to the drawings, in which like reference numerals designate identical or corresponding elements in each of the several views. As used herein the term "distal" refers to that portion of the robotic surgical system, surgical assembly, or component thereof, that is closer to the patient, while the term "proximal" refers to that portion of the robotic surgical system, surgical assembly, or component thereof, that is further from the patient.

Figure 2:
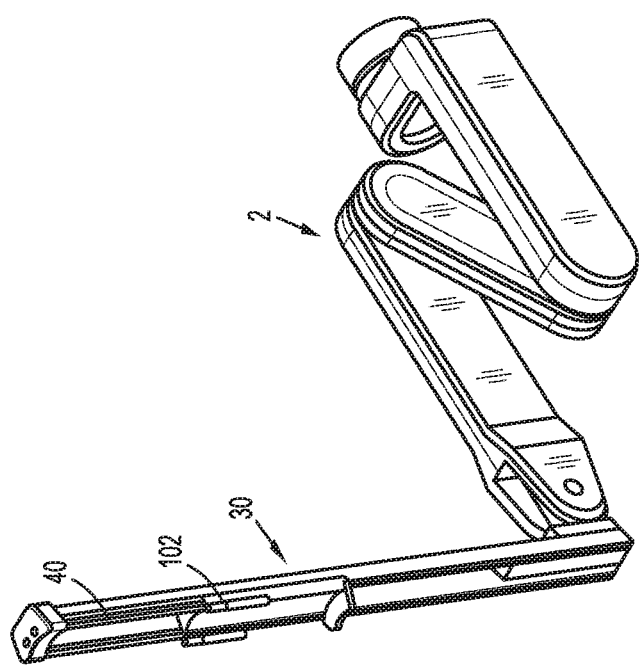
FIG. 2 is a front perspective view of a robotic arm of the robotic surgical assembly of FIG. 1 including an IDU holder.

Referring initially to FIGS. 1 and 2, a surgical system, such as, for example, a robotic surgical system 1, generally includes a plurality of surgical robotic arms 2, 3 having an instrument drive unit (hereinafter, "IDU") 100 and a surgical instrument, or electromechanical instrument, 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the IDUs 100, and thus electromechanical instrument 10 execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may include any number of robotic arms 2, 3, where the additional robotic arms are likewise connected to control device 4 and being telemanipulatable by means of operating console 5. A surgical instrument, for example, electromechanical surgical instrument 10 (including an electromechanical end effector (not shown)), may also be attached to the additional robotic arm.

Figure 3:
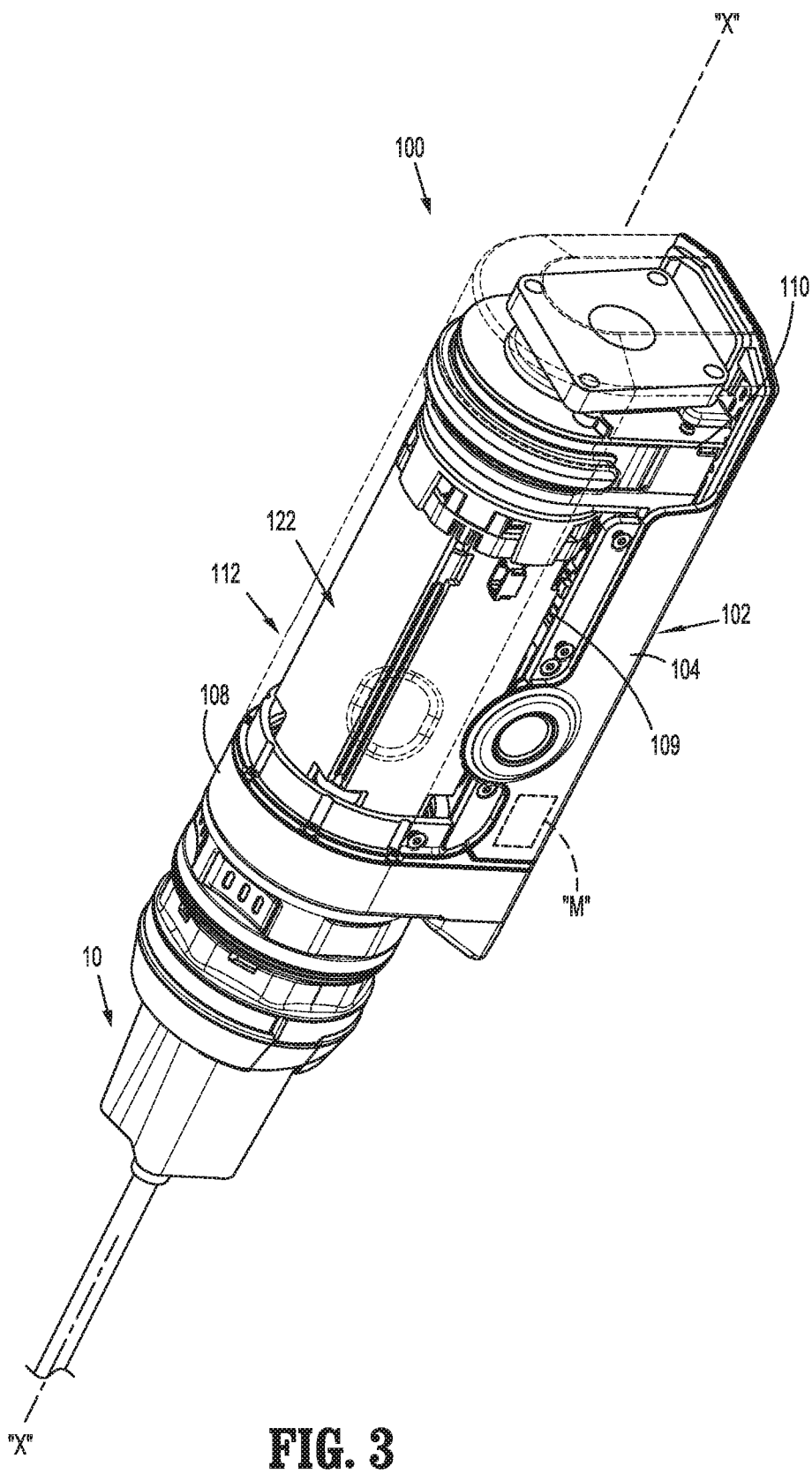
FIG. 3 is a front perspective view of the IDU holder of the robotic surgical assembly of FIG. 2 with an instrument drive unit and a surgical instrument coupled thereto.

Control device 4 may control a plurality of motors, e.g., motors (Motor 1 . . . n), with each motor configured to drive movement of robotic arms 2, 3 in a plurality of directions. Further, control device 4 may control a motor pack 122 (FIGS. 3-4C) of IDU 100 to drive various operations of surgical instrument 10, and may control a rotation of motor pack 122 of IDU 100 to ultimately rotate surgical instrument 10 along a longitudinal axis "X" of IDU 100 (FIG. 3). In embodiments, each motor of motor pack 122 can be configured to actuate a drive rod or a lever arm to effect operation and/or movement of each electromechanical end effector (not shown) of electromechanical instrument 10.

For a detailed description of the construction and operation of a robotic surgical system, reference may be made to U.S. Pat. No. 8,828,023, and U.S. Patent Application No. 62/341,701, the entire contents of each of which is incorporated by reference herein.

With continued reference to FIGS. 1-3, robotic surgical system 1 includes a surgical assembly 30, which includes an instrument drive unit holder (hereinafter, "IDU holder") 102 coupled with or to robotic arm 2, the IDU 100 is couplable to the IDU holder 102, and the surgical instrument 10 is couplable to the IDU 100. IDU holder 102 of surgical assembly 30 holds IDU 100 and surgical instrument 10 and operably couples IDU 100 to robotic arm 2. IDU holder 102 includes an interface panel or carriage 104 and an outer housing portion 108 extending perpendicularly from an end of carriage 104. Carriage 104 supports or houses a motor "M," which receives controls and power from control device 4. Carriage 104 is slidably mounted onto a rail 40 of robotic arm 2, and may be moved along rail 40 via a motor driven chain or belt (not shown) or the like. IDU 100 is non-rotatably couplable to carriage 104 of IDU holder 10, and thus slides along rail 40 of robotic arm 2 concomitantly with carriage 104.

Figure 4A:
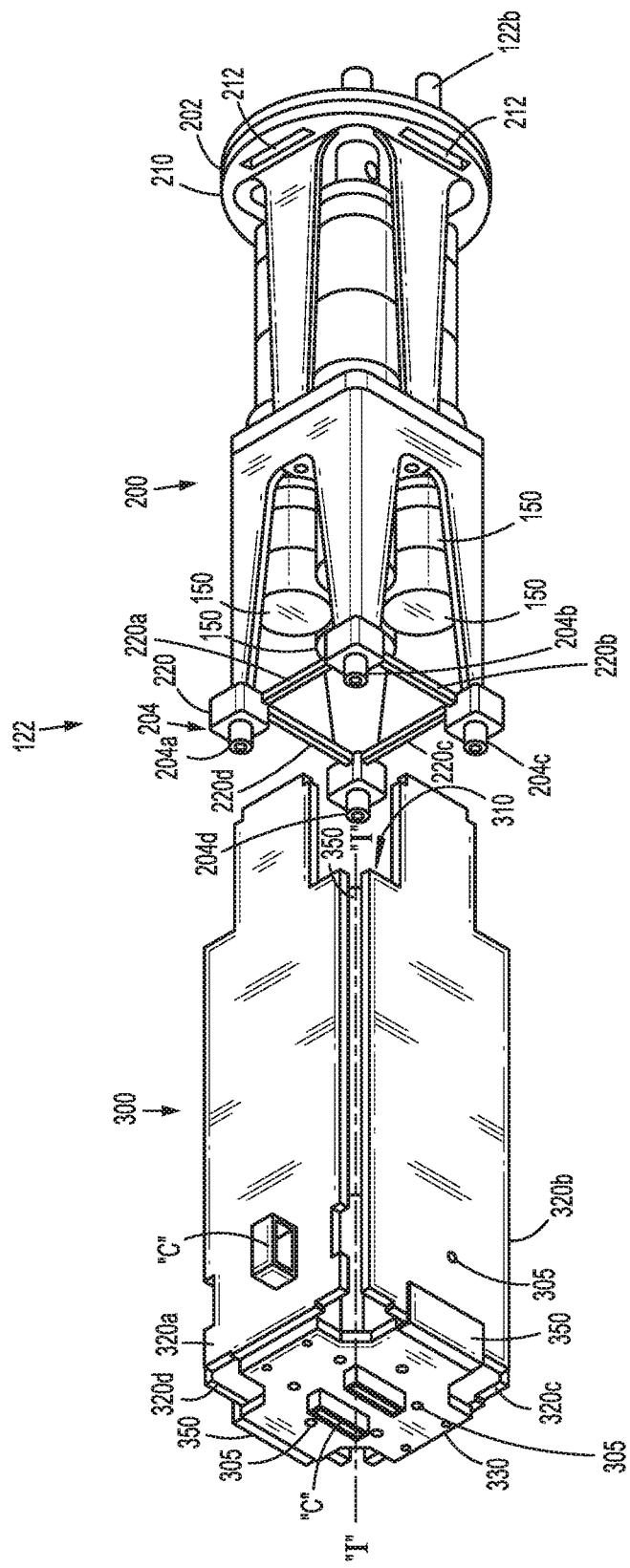
FIG. 4A is a side perspective view of an exemplary embodiment of a motor pack of the instrument drive unit of FIG. 3 with an integrated circuit in a second configuration and separated from the motor assembly.
Figure 4B:
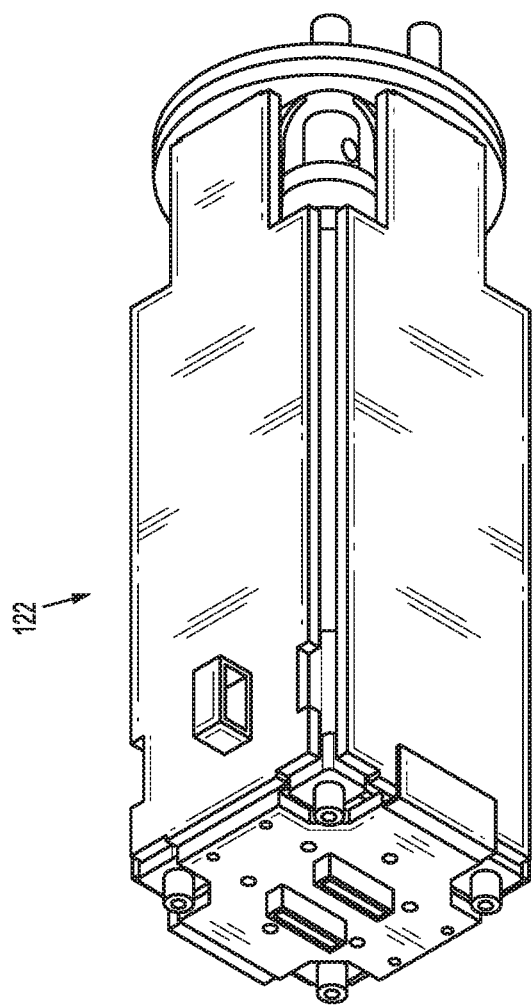
FIG. 4B is a side perspective view of the motor pack of the instrument drive unit of FIG. 4A with the integrated circuit in the second configuration and assembled with the motor assembly.
Figure 4C:
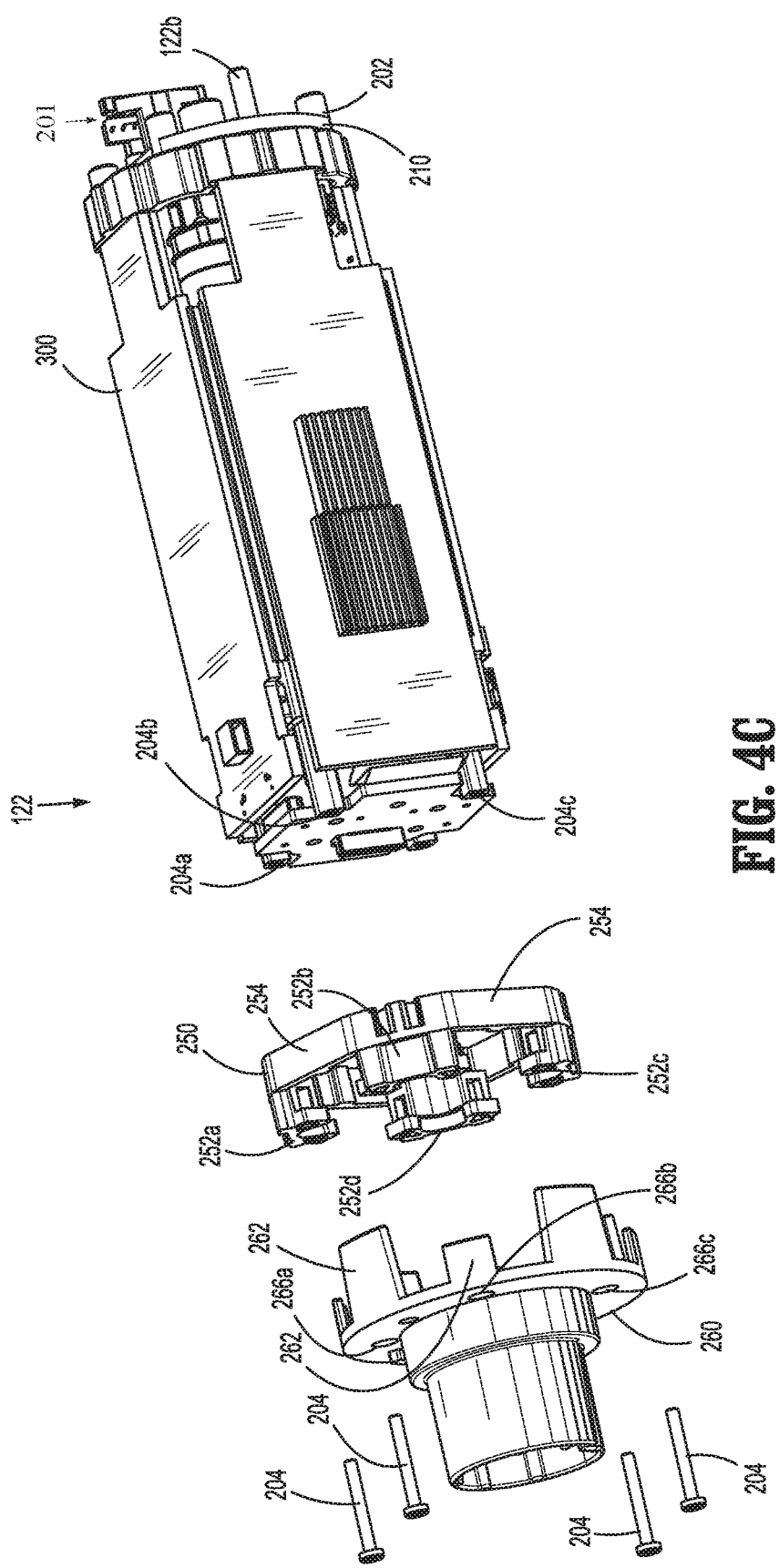
FIG. 4C is a side perspective view of a further exemplary embodiment of the motor pack of the instrument drive unit of FIG. 3 in accordance with the present disclosure, with the integrated circuit in a second configuration and separated from the motor assembly.

Outer housing portion 108 of IDU holder 102 defines a passageway (not shown) therethrough configured to receive a distal end 122*b* of motor pack 122 of IDU 100 (FIGS. 4A-C). As such, when IDU 100 is attached to IDU holder 102, IDU 100 is non-rotatably connected to carriage 104, and the distal end 122*b* of motor pack 122 of IDU 100 is rotatably received within the passageway of outer housing portion 108 of IDU holder 102.

IDU holder 102 further includes control circuitry 109 disposed within carriage 104. Control circuitry 109 is in communication with motor "M" to control the operation of motor "M." Motor "M" is configured to be operably coupled to motor pack 122 of IDU 100 to drive a rotation of motor pack 122 about the longitudinal axis "X" of IDU 100. In some embodiments, control circuitry 109 may be disposed within any of the components of surgical assembly 30.

IDU 100 transfers power and actuation forces from its motors to driven members (not shown) of surgical instrument 10 (FIG. 2) to ultimately drive movement of components of the end effector (not shown) of surgical instrument 10, for example, a movement of a knife blade (not shown) and/or a closing and opening of jaw members (not shown) of the end effector.

With reference to FIGS. 3-4C, a housing cover 112 of IDU 100 (FIG. 3) may be selectively engaged with carriage 104 of IDU holder 102 so as to shroud, cover and protect the inner components of IDU 100 and carriage 104. Housing cover 112 of IDU 100 may have a generally cylindrical configuration, but in some embodiments, housing cover 112 may assume a variety of configurations, such as, for example, squared, triangular, elongate, curved, semi-cylindrical or the like. Housing cover 112 protects or shields various components of IDU 100 including a motor assembly 200, which transfers power and data to components of IDU 100.

With reference to FIGS. 3-4C, motor pack 122 of IDU 100 includes an exemplary motor assembly 200 and an integrated circuit 300. It is envisioned that motor pack 122 may include any number of motors 150 supported in motor assembly 200. It is further envisioned that motors 150 may be arranged in a rectangular formation such that respective drive shafts (not shown) thereof are all parallel to one another and all extending in a common direction. The drive shaft of each motor 150 may operatively interface with a respective driven shaft of surgical instrument 10 to independently actuate the driven shafts of surgical instrument 10.

In the exemplary embodiment illustrated herein, motor pack 122 includes four motors 150 supported in motor assembly 200. Motor assembly 200 may include a distal mounting flange 210 disposed at a distal end 202 thereof, and a proximal mounting structure or frame 220 disposed at a proximal end 204 thereof. Proximal mounting structure 220 includes four struts 220*a-d* spanning between four posts 204*a-d*, wherein the proximal mounting structure 220 defines proximal end 204 of motor assembly 200. While four posts 204*a-d* are shown and described herein, it is contemplated that any number of posts may be provided as needed. Also, while posts 204*a-d* are arranged and illustrated herein in a rectangular configuration, it should be appreciated that any configuration is contemplated and within the scope of the present disclosure.

Proximal mounting structure or frame 220 and distal mounting flange 210 of motor assembly 200 are configured to releasably support integrated circuit 300. More particularly, motor assembly 200 and integrated circuit 300 are configured to nest together, such that integrated circuit 300 is disposed about a portion of motor assembly 200, and motor assembly 200 is received within a cavity 310 defined by integrated circuit 300, as discussed below. In such a configuration, once motor assembly 200 and integrated circuit 300 are assembled to form motor pack 122, motor pack 122 maintains a compactly size.

With reference to FIG. 4C, another exemplary embodiment of motor assembly 201 is illustrated which includes distal mounting flange 210, a proximal mounting cap 250 and a constrainer 260. Proximal mounting cap 250 is configured to sit and nest over integrated circuit 300, and includes four engagement regions 252*a-d* configured to correspond with posts 204*a-d*, respectively. Constrainer 260 is configured to sit and nest over proximal mounting cap 250 and integrated circuit 300, where at least one clip feature 262 selectively engages at least one wall 254 of proximal mounting cap 250. In an embodiment, a screw 264 passed through a respective screw hole 266*a-d* of constrainer 260 and a respective engagement region 252*a-d*, and threadably engages a respective post 204*a-d*, thus securing constrainer 260 and proximal mounting cap 250 to posts 204*a-d*. It should be appreciated that the motor assembles 200, 201 operate similarly with respect to integrated circuit 300 and robotic surgical system 1, where differences and distinctions are noted herein.

Integrated circuit 300 includes a plurality of walls or circuit boards 320*a-d* and a nexus or hub 330 (FIG. 4A), where each circuit board 320*a-d* is coupled, either directly or indirectly, to nexus 330. As illustrated in FIG. 5, nexus 330 is coupled on a first side 331*a* thereof to a first circuit board 320*a*, and coupled on a second side 331*b* thereof to a second circuit board 320*b*. Integrated circuit 300 includes a third circuit board 320*c* and a fourth circuit board 320*d* that are coupled on opposing sides of second circuit board 320*b*. It should be appreciated that circuit boards 320*a-d* and nexus 330 of integrated circuit 300 may be configured in any number of structural combinations, such as, for example, first, second, third, and fourth circuit boards 320*a-d* being coupled, side-by-side, where one of first, second, third, or fourth circuit board 320*a-d* is further coupled to one side of the first, second, third, or fourth side 331*a-d* of nexus 330. In another exemplary embodiment, first and third circuit boards 320*a*, 320*c* may be coupled to first and third sides 331*a*, 331*c* of nexus 330, and second and fourth circuit boards 320*b*, 320*d* may be coupled to second and fourth sides 331*b*, 331*d* of nexus 330. Second circuit board 320*b* has low electrical noise, whereas third and fourth circuit boards 320*c*, 320*d* have relatively high electrical noise.

It is envisioned that each circuit board 320*a-d* and nexus 330 of the integrated circuit 300 may include a printed circuit board assembly ("PCBA"), respectively, having a rigid structure. Further, circuit boards 320*a-d* and nexus 330 of integrated circuit 300 may be mechanically and electrically coupled to one another via at least one integral flex circuit 350, such that circuit boards 320*a*-*d* and nexus 330 are flexibly coupled therebetween. Use of integral flex circuit 350 between circuit boards 320*a*-*d* and nexus 330 enable integrated circuit 300 to be manufactured using PCB origami such that integrated circuit 300 is transitionable between a variety of geometric configurations. In an embodiment, it is contemplated that integral flex circuit 350 may include multiple flex circuits, electrical connectors, or ribbon cables which interconnect circuit boards 320*a*-*d* and nexus 330.

More particularly, during manufacturing, circuit boards 320*a*-*d* and nexus 330 may flex about integral flex circuit 350, with respect to one another, such that integrated circuit 300 is transitionable between a first, open, generally planar configuration (FIG. 6), and a second, three-dimensional configuration (FIGS. 4A and 4B). It should be appreciated that as integrated circuit 300 transitions between the first and second configurations, integrated circuit 300 utilizes PCB origami to achieve an advantage configuration, as discussed herein. As an exemplary embodiment, in the second configuration circuit boards 320*a*-*d* form a rectangular structure which defines a cavity 310, where cavity 310 may be configured to receive motor assembly 200 therein. It is further envisioned that, in the second configuration of the integrated circuit 300, a longitudinal axis "I" (FIG. 4A) defined by cavity 310 may be transverse to a plane defined by nexus 330. In some embodiments, integral flex circuit 350 may be pre-formed into a fixed, yet flexible shape or configured as hinges.

With integrated circuit 300 in the second configuration (FIGS. 4A-4C), a distal end 322*a*-*d* of at least one circuit board 320*a*-*d* (FIG. 5) may be engagable with a respective elastomeric isolator 212 disposed on the distal mounting flange 210 of motor assembly 200. It should be appreciated that one or more elastomeric isolators 212 may be disposed in any desired radial position about distal mounting flange 210 to accommodate the distal ends 322*a*-*d* of a given circuit board 320*a*-*d* while integrated circuit 300 is in the second configuration. It is further envisioned that elastomeric isolators 212 may be configured to interconnect integrated circuit 300 with a larger electromechanical assembly, such as, for example, motor assembly 200, inner shell 120, IDU 100, robotic arm 2, and/or robotic surgical system 1.

Integrated circuit 300 transfers control signals from control device 4 of surgical system 1 to various electric components of IDU 100. For example, integrated circuit 300 may be electrically and mechanically coupled to various motors, torque sensors, accelerometers, temperature sensors, pressure sensors, position sensors, visual indicators (e.g., LEDs), or any other suitable electrical component of IDU 100. Integrated circuit 300 may include an RFID or the like to identify the type of surgical instrument attached to IDU 100. Further, first printed circuit board 320*a* transfers data corresponding to the electrical components of the IDU 100 and/or surgical instrument 10 to the second printed circuit board 320*b* via nexus 330. Additionally or alternately, second printed circuit board 320*b* may transfer data corresponding to the electrical components of IDU 100 and/or surgical instrument 100 to first printed circuit board 320*a* via nexus 330. Third and fourth circuit boards 320*c*, 320*d* transfer power to nexus 330 for powering the various electrical components of IDU 100 and/or surgical instrument 10. Accordingly, second circuit board 320*b* is configured as a microprocessor board and third and fourth circuit boards 320*c*, 320*d* are configured as motor and sensor boards. Nexus 330 is configured to receive and regulate power. First circuit board 320*a* ultimately couples to surgical instrument 10 to receive data collected by various electrical components of surgical instrument 10. It is contemplated that first circuit board 320*a* has an isolation barrier that extends across an intermediate portion thereof.

Integrated circuit 300, which incorporates integral flex circuits or ribbon cables 350, not only provides for ease of manufacturing and ease of assembly, but further provides for an improved mechanical and electrical coupling of circuit boards 320*a*-*d* and nexus 330. It should be appreciated that integrated circuit 300, which incorporates integral flex circuit 350, reduces the need to reserve dedicated space for interconnect solder pin areas for flex ribbon, and their respective accompanying components. As such, the working area of integrated circuit 300 is increased and the assembly process is expedited and simplified by reducing the soldering and testing procedure. Further still, utilization of an integral flex circuit 350 eliminated the need to use multiple connectors, thus providing an optimal, low-resistance, and discrete communication and power transmission path between circuit boards 320*a*-*d*, nexus 330, and ancillary electrical components coupled thereto.

With continued reference to FIGS. 4A-5, it is further envisioned that integrated circuit 300 may include a plurality of vent holes 305 extending through a thickness of a respective circuit board 320*a*-*d* and/or nexus 330. Vent holes 305 provide for the ventilation and dissipation of heat generated by integrated circuit 300 and/or motor assembly 200 of motor pack 122. Vent holes 305 provide a passage through which a fluid (e.g., air) may flow through, such that cooling of integrated circuit 300 and/or motor assembly 200 may be increased. It is further envisioned that vent holes 305 may facilitate and/or maintain the sterility of the operative field, by permitting the creation of a negative pressure through IDU 100.

Integrated circuit 300 may further include one or more power and/or electrical connectors "C" disposed on at least one of circuit board 320*a*-*d* and/or nexus 330. Connectors "C" may represent any means known in the art to transmit and/or transfer power and/or data between electrical and/or electromechanical components, such as, for example, wired or wireless connectors, including, for example, Bluetooth, radio frequency identification (RFID), Near Field Communication (NFC), ZigBee, etc. It is envisioned that connectors "C" may be configured to interconnect integrated circuit 300 with a larger electromechanical assembly, such as, for example, motor assembly 200, inner shell 120, IDU 100, robotic arm 2, and/or robotic surgical system 1.

With reference to FIGS. 3-5, an exemplary assembly of motor pack 122, and IDU 100, will be briefly described. Integrated circuit 300 may be manufactured in the first, planar configuration (FIG. 5). During assembly of the motor pack 122, the PCB origami of integrated circuit 300 facilitates integrated circuit 300 to be folded along integral flex circuits 350 into the second, three-dimensional configuration, such that cavity 310 is defined by circuit boards 320*a*-*d*. Motor assembly 200 of motor pack 122 is insertable into cavity 310, such that nexus 330 of integrated circuit 300 is in near approximation with and/or supported by proximal mounting structure 220, or alternatively proximal mounting cap 250 of motor assembly 201 is nested upon nexus 330 and constrainer 260 is nested upon proximal mounting cap 250, and distal ends 322*a*-*d* of circuit boards 320*a*-*d* of integrated circuit 300 are coupled with elastomeric isolators 212 of distal mounting flange 210. Assembled and coupled integrated circuit 300 and motor assembly 200, or motor assembly 201, make up motor pack 122 of IDU 100. Motor pack 122 may be engaged with IDU 100, where IDU 100 is engaged with carriage 104 of IDU holder 102. Housing cover 112 of IDU 100 may be engaged with carriage 104, enclosing motor pack 122 and IDU 100 as described above, and thus IDU 100 is coupled with robotic arm 2.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. An integrated circuit of a robotic surgical system, the integrated circuit comprising:
    a nexus;
    first and second circuit boards each of which being electrically and mechanically coupled to the nexus on opposing sides of the nexus; and
    third and fourth circuit boards each of which being electrically and mechanically coupled to the second circuit board on opposing sides of the second circuit board, wherein the first, second, third, and fourth circuit boards are parallel with one another and extend distally from the nexus when the integrated circuit is in an assembled configuration, wherein each of the first circuit board, the second circuit board, the third circuit board, and the fourth circuit board has a distal end portion configured to selectively mechanically and electrically engage a motor assembly of a motor pack of an instrument drive unit.

2. The integrated circuit of claim 1, wherein the first, second, third, and fourth circuit boards and the nexus are coupled to one another to define a cavity when the integrated circuit is in the assembled configuration.

3. The integrated circuit of claim 2, wherein the cavity is configured to receive the motor assembly of the motor pack via a distal opening collectively defined by the distal end portion of each of the first, second, third, and fourth circuit boards.

4. The integrated circuit of claim 2, wherein in the assembled configuration, a longitudinal axis defined by the cavity is transverse to a plane defined by the nexus.

5. The integrated circuit of claim 1, wherein the integrated circuit is configured to transition between the assembled configuration and a pre-assembled configuration, in which the first, second, third, and fourth circuit boards and the nexus are substantially coplanar.

6. The integrated circuit of claim 1, wherein the nexus, the first circuit board, the second circuit board, the third circuit board, and the fourth circuit board are printed circuit boards.

7. The integrated circuit of claim 1, wherein at least one of the nexus, the first circuit board, the second circuit board, the third circuit board, or the fourth circuit board defines at least one ventilation hole therethrough.

8. The integrated circuit of claim 1, wherein each of the first circuit board and the second circuit board has a proximal end portion mechanically and electrically coupled with the nexus.

9. The integrated circuit of claim 1, wherein the distal end portion of each of the first circuit board, the second circuit board, the third circuit board, and the fourth circuit board is configured to selectively mechanically and electrically engage a distal mounting flange of the motor assembly.

10. The integrated circuit of claim 1, wherein in the assembled configuration, the first, second, third, and fourth circuit boards collectively define a central longitudinal axis that is transverse to a plane defined by the nexus.

11. An instrument drive unit comprising:
    a housing cover; and
    a motor pack configured for receipt in the housing cover and including:
        an integrated circuit including a nexus, a first circuit board, and a second circuit board, the first and second circuit boards being electrically and mechanically coupled to the nexus on opposing sides of the nexus, wherein the first and second circuit boards are parallel with one another and extend distally from the nexus when the integrated circuit is in an assembled configuration; and
        a motor assembly configured for receipt in the integrated circuit and including:
            at least one motor received in the integrated circuit; and
            a distal mounting flange, the first and second circuit boards each having a distal end portion configured to mechanically and electrically engage the distal mounting flange.

12. The instrument drive unit of claim 11, wherein the integrated circuit further includes third and fourth circuit boards each of which being electrically and mechanically coupled to the second circuit board on opposing sides of the second circuit board.

13. The instrument drive unit of claim 12, wherein the first, second, third, and fourth circuit boards are parallel with one another and extend distally from the nexus when the integrated circuit is in the assembled configuration.

14. The instrument drive unit of claim 12, wherein the first, second, third, and fourth circuit boards and the nexus are coupled to one another to define a cavity when the integrated circuit is in the assembled configuration.

15. The instrument drive unit of claim 14, wherein the cavity is configured to receive the motor assembly via a distal opening collectively defined by the distal end portion of each of the first and second circuit boards and a distal end portion of each of the third and fourth circuit boards.

16. The instrument drive unit of claim 12, wherein the integrated circuit is configured to transition between the assembled configuration and a pre-assembled configuration, in which the first, second, third, and fourth circuit boards and the nexus are substantially coplanar.

17. The instrument drive unit of claim 2, wherein in the assembled configuration, the first, second, third, and fourth circuit boards collectively define a central longitudinal axis that is transverse to a plane defined by the nexus.

18. The instrument drive unit of claim 1, wherein at least one of the nexus, the first circuit board, or the second circuit board includes at least one electrical connector configured to electrically interconnect the nexus, the first circuit board, or the second circuit board with at least one electrical component of the instrument drive unit.

\* \* \* \* \*